United States Patent
Freid et al.

(10) Patent No.: US 6,964,664 B2
(45) Date of Patent: Nov. 15, 2005

(54) SYSTEM AND METHOD FOR STABILIZING THE HUMAN SPINE WITH A BONE PLATE

(75) Inventors: Jim Freid, Austin, TX (US); Michael E. Landry, Austin, TX (US); Erik J. Wagner, Austin, TX (US)

(73) Assignee: Spinal Concepts Inc., Austin, TX (US)

( * ) Notice: Subject to any disclaimer, the term of this patent is extended or adjusted under 35 U.S.C. 154(b) by 210 days.

(21) Appl. No.: 10/015,206

(22) Filed: Nov. 19, 2001

(65) Prior Publication Data

US 2002/0045898 A1 Apr. 18, 2002

Related U.S. Application Data

(63) Continuation of application No. 09/479,458, filed on Jan. 6, 2000, now Pat. No. 6,331,179.

(51) Int. Cl.[7] ............................................. A61B 17/58
(52) U.S. Cl. .............................. 606/61; 606/69; 606/73
(58) Field of Search ............................. 606/61, 69, 73, 606/70, 71, 72, 60

(56) References Cited

U.S. PATENT DOCUMENTS

| | | | |
|---|---|---|---|
| 4,124,235 A | * | 11/1978 | Grahl et al. ................ 285/340 |
| 4,388,921 A | | 6/1983 | Sutter et al. |
| 4,401,112 A | | 8/1983 | Rezaian |
| 4,433,677 A | | 2/1984 | Ulrich et al. |
| 4,492,226 A | | 1/1985 | Belykh et al. |
| 4,501,269 A | | 2/1985 | Bagby |
| 4,503,848 A | | 3/1985 | Caspar et al. |
| 4,570,618 A | | 2/1986 | Wu |
| 4,604,995 A | | 8/1986 | Stephens et al. |
| 4,641,636 A | | 2/1987 | Cotrel |
| 4,643,178 A | | 2/1987 | Nastari et al. |
| 4,743,256 A | | 5/1988 | Brantigan |
| 4,763,644 A | | 8/1988 | Webb |
| 4,805,602 A | | 2/1989 | Puno et al. |
| 4,834,757 A | | 5/1989 | Brantigan |

(Continued)

FOREIGN PATENT DOCUMENTS

| | | |
|---|---|---|
| EP | WO 88/03781 | 6/1988 |
| EP | 0578320 A1 | 1/1994 |
| EP | 0778007 A1 | 6/1997 |
| EP | WO 98/14142 | 4/1998 |
| FR | 2732887 A1 | 10/1996 |
| FR | 2736535 A1 | 1/1997 |

*Primary Examiner*—Pedro Philogene
(74) *Attorney, Agent, or Firm*—Beth A. Vrioni

(57) ABSTRACT

A spinal plate system and method for fixation of the human spine is provided. In an embodiment, the spinal fixation system includes a plate, a coupling member, a locking system for substantially locking the coupling member in a desired position, and an anchoring system to secure the coupling member in the locking system. The plate may have a hole that allows the coupling member to couple the plate with a bone. At least a portion of the coupling member may swivel in the hole so that a bottom end of the member may extend at a plurality of angles substantially oblique to the plate. The locking system may lock the coupling member in desired positions relative to the plate. The anchoring system may secure the coupling member in the locking system to inhibit the coupling system from detaching from the locking system when stressed. An assembly tool may be used to engage and disengage the anchoring system during the installation or removal of the spinal fixation system.

62 Claims, 11 Drawing Sheets

U.S. PATENT DOCUMENTS

| | | | |
|---|---|---|---|
| 4,878,915 A | 11/1989 | Brantigan | |
| 4,887,596 A | 12/1989 | Sherman | |
| 4,946,458 A | 8/1990 | Harms et al. | |
| 4,950,269 A | 8/1990 | Gaines, Jr. | |
| 4,961,740 A | 10/1990 | Ray et al. | |
| 4,966,600 A | 10/1990 | Songer et al. | |
| 4,987,892 A | 1/1991 | Krag et al. | |
| 5,005,562 A | 4/1991 | Cotrel | |
| 5,026,373 A | 6/1991 | Ray et al. | |
| 5,047,029 A | 9/1991 | Aebi et al. | |
| 5,053,036 A | * 10/1991 | Perren et al. | 606/69 |
| 5,055,104 A | 10/1991 | Ray | |
| 5,074,864 A | 12/1991 | Cozad et al. | |
| 5,102,412 A | 4/1992 | Rogozinski | |
| 5,108,399 A | 4/1992 | Eitenmuller et al. | |
| 5,108,446 A | 4/1992 | Wagner et al. | |
| 5,116,340 A | 5/1992 | Songer et al. | |
| 5,123,926 A | 6/1992 | Pisharodi | |
| 5,127,912 A | 7/1992 | Ray et al. | |
| 5,129,388 A | 7/1992 | Vignaud et al. | |
| 5,129,904 A | 7/1992 | Illi | |
| 5,147,359 A | 9/1992 | Cozad et al. | |
| 5,154,718 A | 10/1992 | Cozad et al. | |
| 5,171,278 A | 12/1992 | Pisharodi | |
| 5,176,678 A | 1/1993 | Tsou | |
| 5,176,680 A | 1/1993 | Vignaud et al. | |
| 5,181,917 A | 1/1993 | Rogozinski | |
| 5,192,321 A | 3/1993 | Strokon | |
| 5,192,327 A | 3/1993 | Brantigan | |
| 5,201,734 A | 4/1993 | Cozad et al. | |
| 5,242,445 A | 9/1993 | Ashman | |
| 5,242,448 A | 9/1993 | Pettine et al. | |
| 5,246,442 A | 9/1993 | Ashman et al. | |
| 5,261,909 A | 11/1993 | Sutterlin et al. | |
| 5,263,953 A | 11/1993 | Bagby | |
| 5,281,222 A | 1/1994 | Allard et al. | |
| 5,282,801 A | 2/1994 | Sherman | |
| 5,290,312 A | 3/1994 | Kojimoto et al. | |
| 5,290,494 A | 3/1994 | Coombes et al. | |
| 5,303,718 A | 4/1994 | Krajicek | |
| 5,304,179 A | 4/1994 | Wagner | |
| 5,306,307 A | 4/1994 | Senter et al. | |
| 5,306,309 A | 4/1994 | Wagner et al. | |
| 5,312,405 A | 5/1994 | Korotko et al. | |
| 5,312,410 A | 5/1994 | Miller et al. | |
| 5,318,566 A | 6/1994 | Miller | |
| 5,336,223 A | 8/1994 | Rogers | |
| 5,336,240 A | 8/1994 | Metzler et al. | |
| 5,344,422 A | 9/1994 | Frigg | |
| 5,348,026 A | 9/1994 | Davidson | |
| 5,357,983 A | 10/1994 | Mathews | |
| 5,360,429 A | 11/1994 | Jeanson et al. | |
| 5,360,431 A | 11/1994 | Puno et al. | |
| 5,361,766 A | 11/1994 | Nichols et al. | |
| 5,364,399 A | 11/1994 | Lowery et al. | |
| 5,380,325 A | 1/1995 | Lahille et al. | |
| 5,390,683 A | 2/1995 | Pisharodi | |
| 5,395,374 A | 3/1995 | Miller et al. | |
| 5,397,364 A | 3/1995 | Kozak et al. | |
| 5,403,315 A | 4/1995 | Ashman | |
| 5,405,391 A | 4/1995 | Hednerson et al. | |
| 5,415,658 A | 5/1995 | Kilpela et al. | |
| 5,417,690 A | 5/1995 | Sennett et al. | |
| 5,423,820 A | 6/1995 | Miller et al. | |
| 5,423,825 A | 6/1995 | Levine | |
| 5,425,772 A | 6/1995 | Brantigan | |
| 5,466,237 A | 11/1995 | Byrd, III et al. | |
| 5,474,555 A | 12/1995 | Puno et al. | |
| 5,480,437 A | 1/1996 | Draenert | |
| 5,484,437 A | 1/1996 | Michelson | |
| 5,489,307 A | 2/1996 | Kuslich et al. | |
| 5,489,308 A | 2/1996 | Kuslich et al. | |
| 5,496,318 A | 3/1996 | Howland et al. | |
| 5,501,684 A | 3/1996 | Schlapfer et al. | |
| 5,505,732 A | 4/1996 | Michelson | |
| 5,507,746 A | 4/1996 | Lin | |
| 5,514,180 A | 5/1996 | Heggeness et al. | |
| 5,520,690 A | 5/1996 | Errico et al. | |
| 5,522,899 A | 6/1996 | Michelson | |
| 5,527,341 A | 6/1996 | Gogolewski et al. | |
| 5,531,746 A | 7/1996 | Errico et al. | |
| 5,531,751 A | 7/1996 | Schultheiss et al. | |
| 5,536,270 A | 7/1996 | Songer et al. | |
| 5,536,271 A | 7/1996 | Daly et al. | |
| 5,545,165 A | 8/1996 | Biedermann et al. | |
| 5,549,608 A | 8/1996 | Errico et al. | |
| 5,549,612 A | 8/1996 | Yapp et al. | |
| 5,554,157 A | 9/1996 | Errico et al. | |
| 5,563,124 A | 10/1996 | Damien et al. | |
| 5,569,248 A | 10/1996 | Mathews | |
| 5,569,253 A | 10/1996 | Farris et al. | |
| 5,571,192 A | 11/1996 | Schonhoffer | |
| 5,575,792 A | 11/1996 | Errico et al. | |
| 5,578,033 A | 11/1996 | Errico et al. | |
| 5,578,034 A | 11/1996 | Estes | |
| 5,584,834 A | 12/1996 | Errico et al. | |
| 5,586,984 A | 12/1996 | Errico et al. | |
| 5,593,409 A | 1/1997 | Michelson | |
| 5,601,553 A | 2/1997 | Trebing et al. | |
| 5,601,556 A | 2/1997 | Pisharodi | |
| 5,603,713 A | 2/1997 | Aust et al. | |
| 5,607,424 A | 3/1997 | Tropiano | |
| 5,607,425 A | 3/1997 | Rogozinski | |
| 5,607,426 A | 3/1997 | Ralph et al. | |
| 5,607,428 A | 3/1997 | Lin | |
| 5,607,430 A | 3/1997 | Bailey | |
| 5,609,592 A | 3/1997 | Brumfield et al. | |
| 5,609,593 A | 3/1997 | Errico et al. | |
| 5,609,594 A | 3/1997 | Errico et al. | |
| 5,609,596 A | 3/1997 | Pepper | |
| 5,609,635 A | 3/1997 | Michelson | |
| 5,609,636 A | 3/1997 | Kohrs et al. | |
| 5,611,800 A | 3/1997 | Davis et al. | |
| 5,611,801 A | 3/1997 | Songer | |
| 5,613,967 A | 3/1997 | Engelhardt et al. | |
| 5,616,144 A | 4/1997 | Yapp et al. | |
| 5,620,443 A | 4/1997 | Gertzbein et al. | |
| 5,624,441 A | 4/1997 | Sherman et al. | |
| 5,626,579 A | 5/1997 | Muschler et al. | |
| 5,628,740 A | 5/1997 | Mullane | |
| 5,628,756 A | 5/1997 | Barker, Jr. et al. | |
| 5,630,816 A | 5/1997 | Kambin | |
| 5,632,747 A | 5/1997 | Scarborough et al. | |
| 5,634,925 A | 6/1997 | Urbanski | |
| 5,643,260 A | 7/1997 | Doherty | |
| 5,643,264 A | 7/1997 | Sherman et al. | |
| 5,643,265 A | 7/1997 | Errico et al. | |
| 5,645,084 A | 7/1997 | McKay | |
| 5,645,544 A | 7/1997 | Tai et al. | |
| 5,645,549 A | 7/1997 | Boyd et al. | |
| 5,645,598 A | 7/1997 | Brosnahan, III | |
| 5,647,873 A | 7/1997 | Errico et al. | |
| 5,649,927 A | 7/1997 | Kilpela et al. | |
| 5,651,283 A | 7/1997 | Runciman et al. | |
| 5,651,789 A | 7/1997 | Cotrel | |
| 5,653,708 A | 8/1997 | Howland | |
| 5,653,709 A | 8/1997 | Frigg | |
| 5,653,763 A | 8/1997 | Errico et al. | |
| 5,658,289 A | 8/1997 | Boucher et al. | |
| 5,658,337 A | 8/1997 | Kohrs et al. | |
| 5,658,516 A | 8/1997 | Eppley et al. | |

| | | | | | | |
|---|---|---|---|---|---|---|
| 5,662,653 A | 9/1997 | Songer et al. | 5,702,449 A | 12/1997 | McKay | |
| 5,665,088 A | 9/1997 | Gil et al. | 5,702,450 A | 12/1997 | Bisserie | |
| 5,665,112 A | 9/1997 | Thal | 5,702,451 A | 12/1997 | Biedermann et al. | |
| 5,665,122 A | 9/1997 | Kambin | 5,702,452 A | 12/1997 | Argenson et al. | |
| 5,667,506 A | 9/1997 | Sutterlin | 5,702,453 A | 12/1997 | Rabbe et al. | |
| 5,667,507 A | 9/1997 | Corin et al. | 5,702,454 A | 12/1997 | Baumgartner | |
| 5,667,508 A | 9/1997 | Errico et al. | 5,702,455 A | 12/1997 | Saggar | |
| 5,668,288 A | 9/1997 | Storey et al. | 5,704,936 A | 1/1998 | Mazel | |
| 5,669,909 A | 9/1997 | Zdeblick et al. | 5,704,937 A | 1/1998 | Martin | |
| 5,669,910 A | 9/1997 | Korhonen et al. | 5,707,372 A | 1/1998 | Errico et al. | |
| 5,669,911 A | 9/1997 | Errico et al. | 5,707,395 A | 1/1998 | Li | |
| 5,671,695 A | 9/1997 | Schroeder | 5,709,681 A | 1/1998 | Pennig | |
| 5,672,175 A | 9/1997 | Martin | 5,709,682 A | 1/1998 | Medoff | |
| 5,674,222 A | 10/1997 | Berger et al. | 5,709,683 A | 1/1998 | Bagby | |
| 5,674,295 A | 10/1997 | Ray et al. | 5,709,684 A | 1/1998 | Errico et al. | |
| 5,674,296 A | 10/1997 | Bryan et al. | 5,709,685 A | 1/1998 | Dombrowski et al. | |
| 5,676,665 A | 10/1997 | Bryan | 5,709,686 A | 1/1998 | Talos et al. | |
| 5,676,666 A | 10/1997 | Oxland et al. | 5,713,841 A | 2/1998 | Graham | |
| 5,676,701 A | 10/1997 | Yuan et al. | 5,713,898 A | 2/1998 | Stucker et al. | |
| 5,676,703 A | 10/1997 | Gelbard | 5,713,899 A | 2/1998 | Marnay et al. | |
| 5,681,311 A | 10/1997 | Foley et al. | 5,713,900 A | 2/1998 | Benzel et al. | |
| 5,681,312 A | 10/1997 | Yuan et al. | 5,713,903 A | 2/1998 | Sander et al. | |
| 5,683,391 A | 11/1997 | Boyd | 5,713,904 A | 2/1998 | Errico et al. | |
| 5,683,392 A | 11/1997 | Richelsoph et al. | 5,716,355 A | 2/1998 | Jackson et al. | |
| 5,683,393 A | 11/1997 | Ralph | 5,716,356 A | 2/1998 | Biedermann et al. | |
| 5,683,394 A | 11/1997 | Rinner | 5,716,357 A | 2/1998 | Rogozinski | |
| 5,688,272 A | 11/1997 | Montague et al. | 5,716,358 A | 2/1998 | Ochoa et al. | |
| 5,688,273 A | 11/1997 | Errico et al. | 5,716,359 A | 2/1998 | Ojima et al. | |
| 5,688,274 A | 11/1997 | Errico et al. | 5,716,415 A | 2/1998 | Steffee | |
| 5,688,279 A | 11/1997 | McNulty et al. | 5,716,416 A | 2/1998 | Lin | |
| 5,688,280 A | 11/1997 | Booth, Jr. et al. | 5,720,746 A | 2/1998 | Soubeiran | |
| 5,690,629 A | 11/1997 | Asher et al. | 5,720,747 A | 2/1998 | Burke | |
| 5,690,630 A | 11/1997 | Errico et al. | 5,720,748 A | 2/1998 | Kuslich et al. | |
| 5,690,631 A | 11/1997 | Duncan et al. | 5,720,751 A | 2/1998 | Jackson | |
| 5,690,632 A | 11/1997 | Schwartz et al. | 5,722,977 A | 3/1998 | Wilhelmy | |
| 5,690,633 A | 11/1997 | Taylor et al. | 5,735,853 A * | 4/1998 | Olerud | 606/71 |
| 5,690,842 A | 11/1997 | Panchison | 5,782,832 A | 7/1998 | Larsen et al. | |
| 5,693,046 A | 12/1997 | Songer et al. | 5,807,396 A | 9/1998 | Raveh | |
| 5,693,053 A | 12/1997 | Estes | 5,876,402 A | 3/1999 | Errico et al. | |
| 5,693,100 A | 12/1997 | Pisharodi | 5,904,683 A * | 5/1999 | Pohndorf et al. | 606/61 |
| 5,697,929 A | 12/1997 | Mellinger | 5,954,722 A * | 9/1999 | Bono | 606/61 |
| 5,697,977 A | 12/1997 | Pisharodi | 6,017,345 A | 1/2000 | Richelsoph | |
| 5,700,291 A | 12/1997 | Kuslich et al. | 6,193,721 B1 | 2/2001 | Michelson | |
| 5,700,292 A | 12/1997 | Margulies | 6,235,033 B1 * | 5/2001 | Brace et al. | 606/69 |
| 5,702,391 A | 12/1997 | Lin | 6,261,291 B1 | 7/2001 | Talaber et al. | |
| 5,702,392 A | 12/1997 | Wu et al. | 6,331,179 B1 * | 12/2001 | Freid et al. | 606/61 |
| 5,702,393 A | 12/1997 | Pfaifer | 6,454,769 B2 * | 9/2002 | Wagner et al. | 606/69 |
| 5,702,394 A | 12/1997 | Henry et al. | 6,599,290 B2 | 7/2003 | Bailey et al. | |
| 5,702,395 A | 12/1997 | Hopf | 2002/0058939 A1 | 5/2002 | Wagner et al. | |
| 5,702,396 A | 12/1997 | Hoenig et al. | | | | |
| 5,702,399 A | 12/1997 | Kilpela et al. | * cited by examiner | | | |

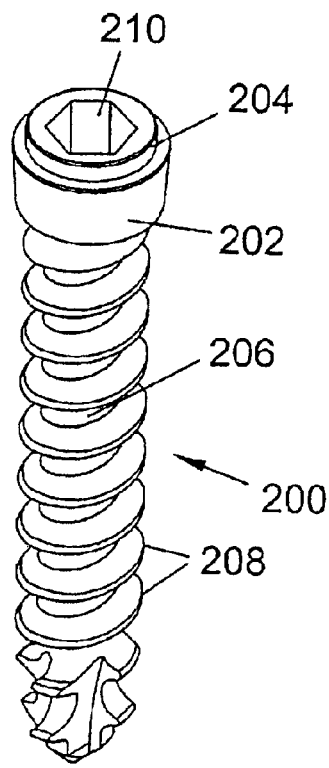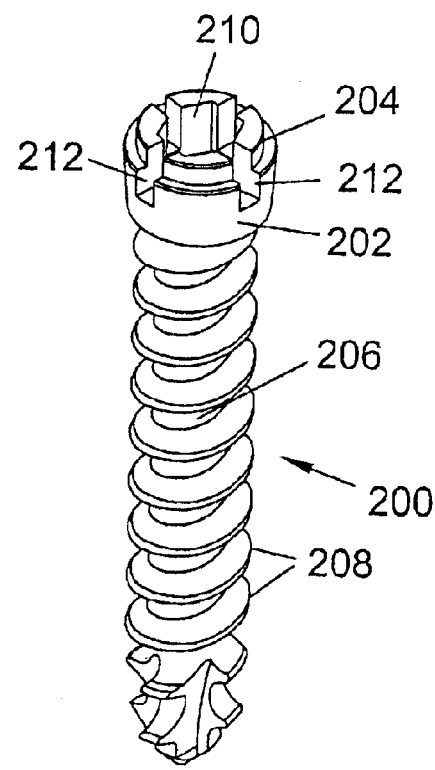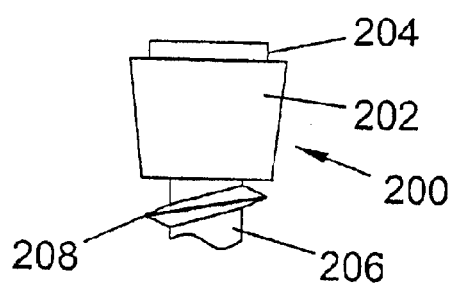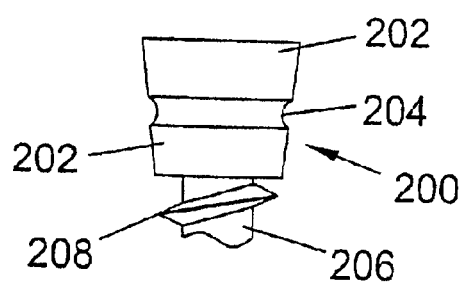
FIG. 15
FIG. 17
FIG. 16
FIG. 18

SYSTEM AND METHOD FOR STABILIZING THE HUMAN SPINE WITH A BONE PLATE

This patent is a continuation of application Ser. No. 09/479,458 filed Jan. 6, 2000, now U.S. Pat, No. 6,331,179.

BACKGROUND OF THE INVENTION

1. Field of the Invention

The present invention generally relates to spinal fixation systems and the like. The present invention also generally relates to a spinal plate system that includes a mechanism for fixably attaching heads of fasteners to a spinal plate.

2. Description of the Related Art

The use of spinal fixation plates for correction of spinal deformities and for fusion of vertebrae is well known. Typically, a rigid plate is positioned to span bones or bone segments that need to be immobilized with respect to one another. Bone screws may be used to fasten the plate to the bones. Spinal plating systems are commonly used to correct problems in the lumbar and cervical portions of the spine, and are often installed posterior or anterior to the spine.

Spinal plate fixation to the cervical portion of the spine may be risky because complications during surgery may cause injury to vital organs, such as the brain stem or the spinal cord. When attaching a fixation plate to a bone, bone screws are placed either bi-cortically (i.e., entirely through the vertebrae such that a portion of the fastener extends into the spinal cord region) or uni-cortically (i.e., the fastener extends into but not through the vertebrae). Uni-cortical positioning of bone screws has grown in popularity because it is generally safer to use. Bi-cortical fasteners are intended to breach the distal cortex for maximum anchorage into the bone; however, this placement of the fasteners may place distal soft tissue structures at risk. Fastener placement is particularly important in anterior cervical plate procedures because of the presence of the spinal cord opposite the distal cortex. Unfortunately, uni-cortical fasteners may move from their desired positions because of the soft texture of the bone marrow. In fact, the portion of the bone surrounding such fasteners may fail to maintain the fasteners in their proper positions. The result is backout of the fastener.

Backout of the fastener is particularly problematic when two fasteners are implanted perpendicular to the plate. When the fasteners are placed in such a manner, backout may occur as a result of bone failure over a region that is the size of the outer diameter of the fastener threads. To overcome this problem, two fasteners may be angled in converging or diverging directions with respect to each other within the bone. The amount of bone that is required to fail before backout may occur is increased by this configuration as compared to fasteners that are implanted in parallel. Although positioning convergent or divergent fasteners in a bone reduces the risk of backout, backout may still occur.

Backout may damage internal tissue structures and cause complications if the dislocated fastener penetrates the tissue structures. For example, if backout occurs, the fastener might breach the esophageal wall of the patient. Such a breach may permit bacterial contamination of surrounding tissues, including critical nerves in and around the spinal cord. Such a breach could be fatal.

In an attempt to reduce the risk of damage to internal tissue structures, some cervical fastener plate systems have uni-cortical fasteners that attach both to the bone and to the plate. If a fastener does backout, the fastener remains connected to the plate so that it does not contact internal tissue structures. U.S. Pat. No. 5,364,399 to Lowery et al. describes one such system and is incorporated by reference as if fully set forth herein. The Lowery et al. plating system includes a locking fastener at each end of the plate. The locking fastener engages the head of the bone screw to trap the fastener within a recess of the plate. Since the locking fastener is positioned over portions of the bone screws, the locking fastener may extend above the upper surface of the plate. Thus, the locking fastener may come into contact with internal tissue structures, such as the esophagus.

Another plating system that includes a fastener-to-plate locking mechanism is the Aline™ Anterior Cervical Plating System sold by Smith & Nephew Richards Inc. in Memphis, Tenn. A description of this system can be found in the Aline™ Anterior Cervical Plating System Surgical Technique Manual by Foley, K. T. et al., available from Smith & Nephew Richards Inc., 9/96, pp. 1–16 and is incorporated by reference as if fully set forth herein. The bone screws of this system have openings within each bone screw head for receiving a lock fastener coaxially therein. Each bone screw may be inserted into a bone such that the head of the fastener is positioned within a hole of a plate placed adjacent to the bone. The head of each bone screw is slotted so that portions of the head are deflected toward the plate during insertion of the lock fastener within the opening of the bone screw. Positioning and inserting a lock fastener within the opening can be difficult due to the small size of the lock fastener. The surgeon may be unable to hold onto the lock fastener without dropping it. If a lock fastener falls into the surgical wound, it may be difficult to retrieve. In some instances, the lock fastener may be unretrievable.

SUMMARY OF THE INVENTION

An implant system may be used to immobilize a portion of a human spine. The implant system may include a plate comprising end holes, midline holes, fasteners, and expandable/contractible rings. The fasteners and rings may include mechanisms for anchoring or locking the fastener heads within the rings to inhibit backout of the fastener.

The end holes extend from an upper surface to a lower surface of the plate. The end holes may be disposed in pairs at opposite ends of the plate. Each end hole receives at least a portion of a head of a fastener. Herein, "fastener" means any elongated member, threaded or non-threaded, which is securable within a bone. Fasteners include, but are not limited to screws, nails, rivets, trocars, pins, and barbs. The fastener may be a bone screw. A fastener may have a fastener head. The fastener head typically includes an opening adapted to mate with a tool. The tool allows the insertion of the fastener into a bone. Each end hole may also be spherically contoured to permit the fastener to be "obliquely angulated" relative to the plate. Herein, "obliquely angulated" means that the fastener may be positioned throughout a wide range of angles relative to an axis that is perpendicular to the plate. Obliquely angulating a fastener into a bone may reduce the risk of backout of the fastener.

The expandable/contractible rings may be sized so that a ring seats within an end hole between the plate and the fastener. The inner surface of each ring may be shaped to mate with a fastener head while the outer surface may be shaped to mate with the inside surface of an end hole. The outer surface of each fastener head may be tapered so that an upper portion of the head is larger than a lower portion of the head. The inner surface of the ring may have a taper that generally corresponds to the taper of the fastener head.

Each ring may also have a gap that extends vertically through the ring to make the ring more readily expandable and contractible. During insertion of the fastener head into the ring, the fastener head exerts force against the ring to expand the ring against the inner surface of the hole. Expanding the ring against the inner surface of the hole may securely fix the fastener to the plate.

The fastener head and the ring may include a locking mechanism to attach the fastener head to the plate. The locking mechanism may inhibit backout of the fastener head from the ring if the fastener loosens in the bone. The locking mechanism may also inhibit the fastener head from contacting adjacent tissue structures since the locking mechanism attaches the fastener head to the plate. In some embodiments, there is tolerance for some freedom of movement in an axial direction between a locking mechanism and a fastener head. The availability of some axial movement may allow the fastener to back out or loosen slightly from the bone during a normal period of adjustment after implantation of a spinal fixation system.

Midline holes may be formed through the plate at various locations along a midline axis extending across the plate. The surface of the plate that surrounds each midline hole may be tapered. Further, the heads of fasteners that may be positioned within the plates may have tapered outer surfaces that generally correspond to the tapered surface of the plate. Thus, when such a fastener head is inserted into a midline hole, the shape of the plate causes the fastener to become fixably attached to the plate in a position that is substantially perpendicular to the plate. Midline holes may be used to attach a bone graft to the bone plate. Oblique angulation of fasteners positioned within the midline holes may not be required.

The bone plate may have one or more spikes located on the surface of the plate that faces the spinal column. Spikes may be disposed in pairs at opposite ends of the plate proximate the end holes. The spikes may be tapped into the bone to help inhibit the bone plate from slipping during surgical implantation.

Prior to surgical implantation of the spinal plate system, the expandable/contractible rings may be placed within the end holes of the plate. The plate may then be positioned adjacent to a portion of the spine that requires spinal fixation. Holes may be drilled and/or tapped at desired angles into portions of the bone underlying the end holes of a plate. Fasteners may be inserted through the end holes into the holes in the bone. The heads of the fasteners may be positioned within the end holes such that the rings surround at least a portion of the heads. The rings may lock the fasteners in place without occupying regions outside of the end holes. Further, since the rings are pre-positioned within the end holes, surgeons do not have to worry that they may drop the rings during insertion of the rings into the end holes of the plate.

In one embodiment, a locking mechanism secures a fastener head to a ring. A locking mechanism may have a top and one or more flexible arms that angle downwards and outwards from the top. The ends of the arms have prongs that are substantially parallel to the top of the locking mechanism. A locking mechanism in a compressed configuration, fits into an opening formed in the head of a fastener. The prongs of the locking mechanism fit within holes located near the bottom of the opening. The holes extend from the outer surface of the head to the opening. When the prongs are positioned in the holes, the prongs extend through the holes so that the locking mechanism is in an extended configuration. The prongs that extend out of the head of the fastener fit within a groove on the inner surface of the ring to enhance the connection between the fastener and the ring.

The locking mechanism may be inserted in the fastener head prior to the surgical procedure to avoid the risk of dropping the locking mechanism during the surgical procedure. An insertion and extraction tool retracts the prongs on the locking mechanism into the head during insertion or extraction of a fastener. The tool may include a handle, a shaft, and a hollow driver head shaped to match a drive section of the opening on the fastener head. Inserting the driver head into the opening slides the head over the locking mechanism and compresses the shafts of the locking mechanism. Compressing the shafts of the locking mechanism retracts the prongs into the fastener head. To insert a fastener into a bone, the user inserts the fastener into the bone until the head is fully inserted in the ring. Removing the driver head from the opening causes the shafts of the locking mechanism to expand outwards so that the prongs extend out of the holes into the fastener head.

To remove a fastener that has a locking mechanism, the user inserts the driver head of the insertion and extraction tool into the opening of the fastener head. The driver head compresses the shafts of the locking mechanism and causes the prongs to retract within the fastener head. The user may then remove the fastener from the bone.

In another embodiment, a tapered fastener head locks into a ring by one or more fingers on the ring that snap into grooves on the fastener head. L-shaped slots cut into the top of the ring may define the fingers. The fingers have springlike action so that the fingers snap into the grooves on the fastener head when a fastener head is inserted into the ring. As the fastener head passes into the ring, the tapered outer surface of the head expands the ring against the inner surface of the plate. When the groove on the fastener head reaches the fingers, the fingers snap into the groove, fixing the fastener in the ring and helping to inhibit backout.

In another embodiment, a fastener head locks to a ring by one or more ridges on the ring that snap into grooves on the fastener head. Notches cut into the top of the ring may form paddles. A ridge may extend along an inside surface of each paddle proximate the top of the ring. The paddles have a springlike action so that the ridges snap into the grooves on the fastener head during insertion of the fastener head into the ring. The ridges of the ring residing within a groove of the fastener head may fix the fastener in the ring and help inhibit backout of the fastener.

An extraction tool module fits over an insertion tool and allows the retraction of the ring ridges from the fastener head. The insertion tool includes a handle, a shaft, and a driver head shaped to match the opening on the fastener head. The extraction module slides over the shaft of the insertion tool. The extraction module may include a handle and an extraction head. The extraction head may include a tip that slides over the fastener head and contacts the ends of the paddles. The outer surface of the tip tapers. As the extraction module is pushed down, the tapered surface of the tip forces the paddles outwards and disengages the ridges on the paddles from the grooves on the fastener head. Disengaging the ridges on the paddles from the grooves on the fastener head allows the fastener to be backed out of the bone.

Using a locking mechanism between the fastener head and the ring may result in a strong connection between the fastener and the plate. Even if the shank of a fastener loosens within the bone, the fastener head will tend to remain within the hole of the plate so as not to protrude from the plate into surrounding body tissue. Allowing some axial freedom of movement for the fastener head in the ring may allow the fastener to back out slightly during an adjustment period after installation of the spinal fixation system.

BRIEF DESCRIPTION OF THE DRAWINGS

Advantages of the present invention will become apparent to those skilled in the art with the benefit of the following detailed description of embodiments and upon reference to the accompanying drawings in which:

FIG. 15 is a perspective view of an embodiment of a fastener.

FIG. 16 is a front view of an embodiment of a fastener head.

FIG. 17 is a perspective view of an embodiment of a fastener.

FIG. 18 is a front view of an embodiment of a fastener head with a groove.

Figure 1:
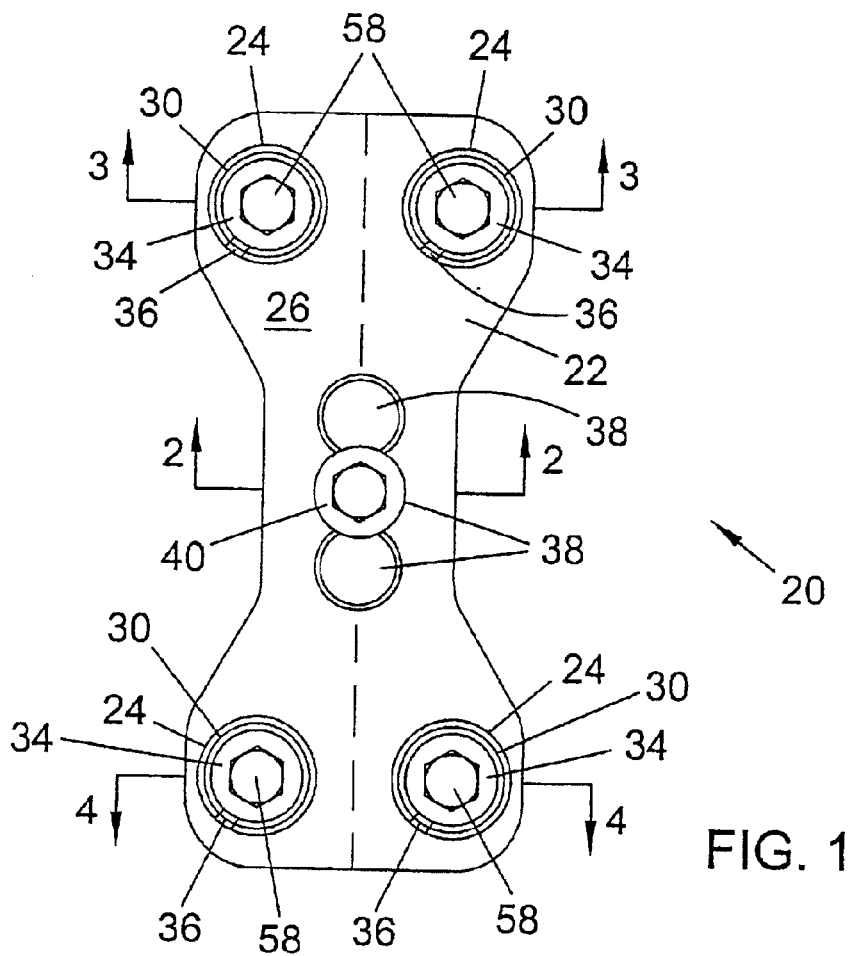
FIG. 1 is a top view of an embodiment of a spinal plating system that may be used for fixation of the human spine.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2:
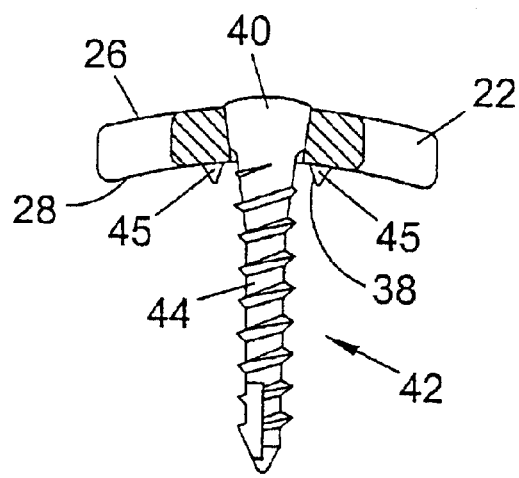
FIG. 2 is a partial cross-sectional view of the spinal plating system taken substantially along line 2—2 of FIG. 1. The fastener is not shown in section.

Referring to the drawings, and particularly to FIG. 1, a spinal plating system is designated generally as 20. The spinal plating system 20 may be used to correct problems in the lumbar and cervical portions of the spine. For example, the spinal plating system 20 may be implanted into the occiput bone that is located at the base of the skull. The spinal plating system 20 may also be installed anterior to the spine. The spinal plating system 20 includes plate 22 that is placed adjacent to a portion of the spine and spans at least two vertebrae. Plate 22 may include four end holes 24, located at corners of the plate. End holes 24 pass vertically through plate 22 such that the holes extend from an upper surface 26 to a lower surface 28 of the plate as depicted in FIG. 2. End holes 24 are configured to receive rings 30. Fasteners 32 fit within the rings 30. Herein, "fastener" means any elongated member, threaded or non-threaded, which is securable within a bone. Fasteners include, but are not limited to screws, nails, rivets, trocars, pins, and barbs. The fastener may be a bone screw. Rings 30 fixedly attach fastener heads 34 of fasteners 32 to plate 22. Gap 36 may exist in each of the rings 30. A gap 36 allows for expansion and contraction of a ring 30. Ring contraction allows a ring 30 to be easily inserted into an end hole 24 of the plate 22.

The spinal plating system 20 may also include one or more central holes 38 that extend vertically through plate 22. One of the central holes 38 may be located at about the mid-point of the plate 22. Head 40 of fastener 42 is positioned within one of the central holes 38. Multiple central holes 38 provide a surgeon with options as to the most desirable location for placement of a fastener 42. Fastener 42 may be used to connect plate 22 to a bone graft (not shown).

FIG. 2 shows a fastener 42 within one of the central holes 38 of plate 22. Fastener 42 may include head 40 and shank 44. The shank 44 extends from the base of head 40. In one embodiment, the inner surface of a central hole 38 tapers so that the hole is larger at upper plate surface 26 than at the lower plate surface 28. The outer surface of the fastener head 40 has a taper that generally corresponds to the taper of the central hole 38. During implantation of a fastener 42 into a bone graft, the shank 44 of the fastener 42 is inserted into a hole that has been formed in the bone graft under hole 38. Because the lower portion of hole 38 is smaller than the upper portion of the fastener head 40, fastener 42 may become locked into place within the central hole 38 once the fastener has been inserted to a desired depth within the bone graft. The bone plate 22 may have spikes 45 extending from the lower plate surface 28.

As shown in FIG. 2, the plate 22 may have a curvature. The curvature may enhance fixation of the plate 22 to a bone. The bone plate 22 may have one or more spikes 45 located on the surface of the plate that faces the bone. The spikes 45 may be disposed in pairs at opposite ends of the plate proximate the end holes 24. The spikes 45 may be tapped into the bone to help inhibit the bone plate 22 from slipping during surgical implantation.

Figure 3:
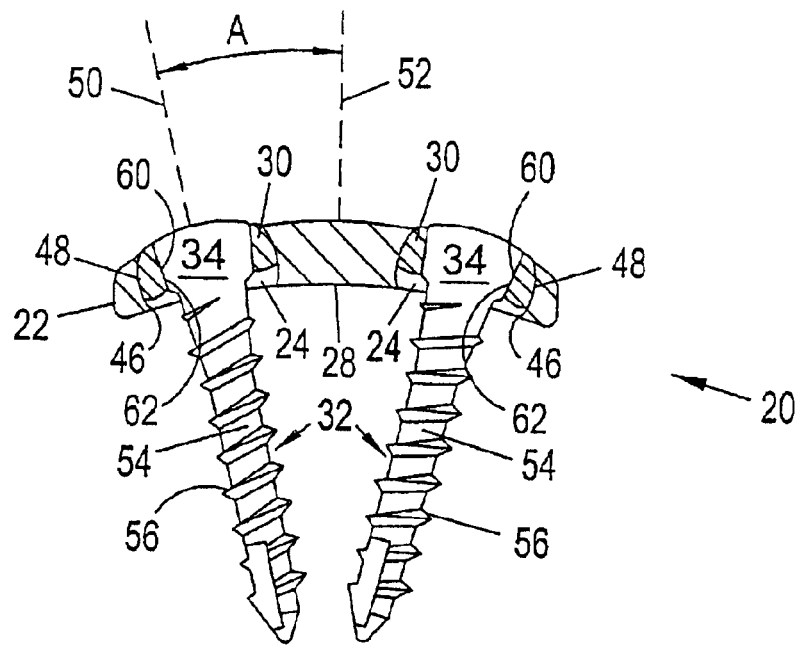
FIG. 3 is a partial cross-sectional view of the spinal plating system taken substantially along line 3—3 of FIG. 1, wherein the fasteners are in a converging orientation within end holes of a plate. The fasteners are not shown in section.
Figure 4:
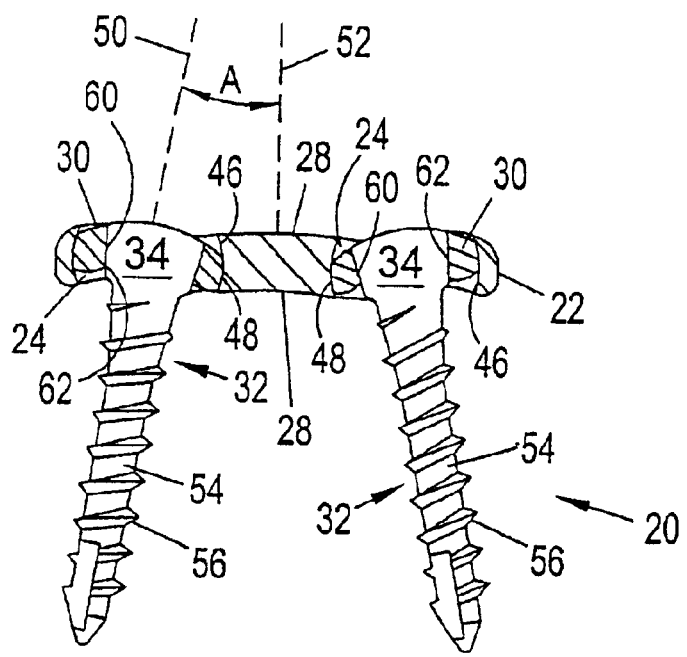
FIG. 4 is a partial cross-sectional view of the spinal plating system taken substantially along line 4—4 of FIG. 1, wherein the fasteners are in a diverging orientation within end holes of a plate 5, the fasteners are not shown in section.

FIG. 3 depicts a cross-sectional view of an embodiment of a spinal plating system 20 wherein a pair of fasteners 32 are in a converging configuration. FIG. 4 depicts a cross-sectional view of an embodiment of a spinal plating system wherein a pair of fasteners 32 are in a diverging configuration. Ring 30 fits into a hole 24 between plate 22 and fastener head 34. Inner surfaces 46 of holes 24 may have arcuate or spherical contours. Outside surfaces 48 of rings 30 may have arcuate or spherical contours that substantially correspond to the contours of the inner surfaces 46 of the holes 24. Having a contoured ring outer surface 48 that substantially corresponds to the contour of the inner hole surface 46 allows a ring 30 positioned in an end hole 24 to be capable of polyaxial rotation within the end hole.

The combination of ring 30 within end hole 24 functions like a ball and socket since the ring may be swiveled or polyaxially rotated within the end hole. The ability of the ring 30 to rotate polyaxially within the end hole 24 allows a fastener 32 to be positioned through the plate 22 at various angles with respect to an axis that is perpendicular to the plate. FIGS. 3 and 4 show angle A for particular fastener configurations. The angle A is defined between the longitudinal axis 50 of the fastener 32 and imaginary axis 52 that is perpendicular to the plate 22. The angle A may range from 0 to about 45 degrees, preferably from about 0 to about 30 degrees, and more preferably from 0 to about 15 degrees.

Fasteners 32 may also be set in positions such that the fasteners are non-planar with respect to a latitudinal plane extending through plate 22. For example, one fastener 32 may be positioned out of the page and another fastener 32 may be positioned into the page, as depicted in FIGS. 3 and 4. Fasteners 32 set in diverging or converging directions in the end holes 24 may reduce the possibility of backout. Further, the use of rings 30 to fixedly attach fasteners 32 to plate 22 may inhibit damage to tissue structures by any fasteners that do loosen within a bone, since such fasteners would remain attached to the plate 22. Fasteners 32 may be placed in uni-cortical positions within a bone since the problem of fastener backout is reduced by having obliquely angulated fasteners in converging or diverging configurations.

Ring 30 may at least partially surrounds head 34 of fastener 32 positioned within end hole 24. A shank 54 of fastener 32 may include threading 56 to allow the fastener to be inserted into a bone when fastener 32 is rotated. As depicted in FIG. 1, fastener head 34 may include a cavity 58 that extends from the top of the head to an inner portion of the head. Cavity 58 may be shaped to receive an end of a tool that inserts or removes the fastener 32 from a bone. The tool end may be in the form of a hex wrench, a star wrench or a screwdriver blade.

Inner surface 60 of ring 30 and outer surface 62 of head 34 may have mating tapered surfaces, as depicted in FIG. 3 and FIG. 4. In one embodiment, the bottom portion of head 34 may be smaller than the upper portion of an unstressed ring 30, while the upper portion of the head may be larger than the upper portion of the ring. As fastener 32 is inserted into a bone, head 34 applies a radial force to ring 30 which causes the ring to expand within the end hole 24. Expanding the ring 30 increases the size of gap 36 and may cause the outside surface 46 of the ring to abut against inner surface 46 of the end hole 24. An interference fit forms between fastener head 34, ring 30, and plate 22 in which these elements fit together such that each element obstructs the movement of the other elements. Hoop stress of ring 30 on head 34 fixedly attaches fastener 32 to plate 22.

Ring 30 may be capable of swiveling within an end hole 24 so that one portion of ring 30 is adjacent to the upper surface 26 of bone plate 22 while another portion of the ring lies adjacent to the lower surface 28 of the bone plate. In one embodiment, ring 30 may sufficiently thin to reside within end hole 24 without extending beyond the upper or lower surface 26, 28 of bone plate 22. The ring 30 and fastener head 34 remain within end hole 24 so that the spinal plating system 20 may have a minimal profile width. Having rings 30 and the fastener heads 34 which do not extend above the upper surface 26 or below the lower surface 28 of plate 22 may prevent the rings and heads from contacting adjacent tissue structures. In other embodiments, however, fasteners 32 may be capable of being angulated relative to bone plate 22 such that the rings 30 extend from the end holes 24 beyond upper and/or lower surfaces of the bone plate.

In one embodiment, the spinal plating system 20 is prepared for surgical implantation by positioning rings 30 within end holes 24. During the surgical procedure, holes may be drilled and tapped into the bones to which plate 22 is to be attached. Plate 22 may be positioned adjacent to the bones and over the holes in the bone. Fasteners 32 may be placed through a ring 30 and into the bone holes. Each fastener 32 may be obliquely angulated into the plate 22. The fasteners 32 may be inserted into the bone until the fastener heads 34 expand the rings 30 against the inner surfaces 46 of the end holes 24; thus fixing the fasteners to the rings, and the rings to the plate 22. If necessary, a fastener 42 may be positioned in one of the central holes 38.

In one embodiment, ring 30 has an outer width that is less than or about equal to the width of an end hole 24 in bone plate 22 at a location between an upper surface 26 and lower surface 28 of the bone plate. The width of each end hole 24 proximate the upper and lower surfaces 26, 28 of bone plate 22 is less than or about equal to an outer width of ring 30. The width of the ring may inhibit a ring positioned in an end hole from falling out of the hole. Prior to surgery, a ring 30 may be positioned within each end hole 24 of bone plate 22. When seated within end hole 24, ring 30 may be capable of swiveling within the hole, but the ring is inhibited from falling out of the hole because of reduced width of the hole proximate the upper and lower surfaces 26, 28 of the plate 22. Alternatively, rings 30 may be manually positioned within end holes 24 during surgery.

Texturing the outer surface 48 of a ring 30 or an inner surface 46 of an end hole 24 may further inhibit movement of a fastener 32 with respect to a bone plate 22. Both surfaces may be textured to more effectively inhibit movement of a fastener 32 with respect to a bone plate 22. During manufacturing procedures, the outer surface 48 of ring 30 and the inner surface defining end hole 24 are formed as relatively smooth surfaces. While the friction between these smooth surfaces tends to be sufficient to maintain fastener 32 in a fixed position with respect to plate 22; under stressful conditions ring 30 may rotate within hole 24. By providing at least one textured surface, the coefficient of friction between the surface defining end hole 24 and ring 30 is increased. The increase in friction between the surface defining end hole 24 and ring 30 may help to inhibit fastener movement relative to plate 22.

Several types of textured surfaces may be used to increase the coefficient of friction between ring 30 and a surface defining end hole 24. In general, any process that transforms a relatively smooth surface into a textured surface having an increased coefficient of friction may be used. Methods for forming a textured surface include, but are not limited to: sanding, forming grooves within a surface, shot peening processes, electric discharge processes, and embedding of hard particles within a surface.

A shot peening process for forming a textured surface is described in U.S. Pat. No. 5,526,664 to Vetter which is incorporated by reference as if set forth herein. In general, a shot peening process involves propelling a stream of hardened balls, typically made of steel, at a relatively high velocity at a surface. To create a pattern upon an area of the surface the stream is typically moved about the surface. The speed by which the stream is moved about the surface determines the type of textured surface formed.

An electrical discharge process is based on the principle of removal of portions of a metal surface by spark discharges. Typically a spark is generated between the surface to be treated and an electrode by creating potential differential between the tool and the electrode. The spark produced tends to remove a portion of the surface disposed between the electrode and the surface. Typically, the electrode is relatively small such that only small portions of the surface are removed. By moving the electrode about the surface numerous cavities may be formed within the surface. Typically these cavities are somewhat pyramidal in shape. Various patterns may be formed within the surface depending on how the electrode is positioned during the discharge. Electric discharge machines are well known in the art. A method for forming a frictional surface within a metal surface using an electric discharge process is described in U.S. Pat. No. 4,964,641 to Miesch et al., which is incorporated by reference as if set forth herein.

Embedding hardened particles in a surface produces a textured surface. A method for embedding hardened particles in a metal surface is described in U.S. Pat. No. 4,768,787 to Shira, which is incorporated by reference as if set forth herein. The method of Shira involves using a laser or other high-energy source to heat the surface such that the surface melts in selected areas. Just before the molten area re-solidifies, a stream of abrasive particles is directed to the area. In this manner some of the particles tend to become embedded within the molten surface. The particles typically have a number of sharp edges that protrude from the surface after the particles have been embedded within the surface.

Any of the above methods of texturing may be used in combination with another method. For example, the inner surface 46 of end hole 24 may be textured using a pattern of grooves. The outer surface 48 of ring 30, however, may be textured using an electrical discharge method. When coupled together the textured inner surface of end hole 24 and ring 30 may interact with each other to provide additional resistance to movement of the ring within the hole.

Figure 5:
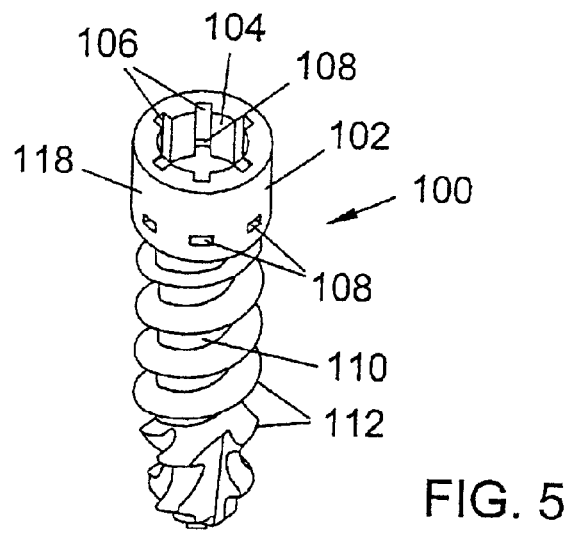
FIG. 5 depicts an embodiment of a fastener with grooves and holes to engage a locking mechanism.

FIG. 5 illustrates an embodiment of fastener 100. The fastener 100 may include fastener head 102, opening 104, optional grooves 106, holes 108, shank 110 and threads 112. Opening 104 accepts a drive tool, such as drive tool 114, which is described below. The opening 104, grooves 106 and holes 108 accept locking mechanism 116, as described below. Holes 108 extend from the outer surface 118 of head 102 to the opening 104. In one embodiment, the outer surface 118 is substantially cylindrical. In another embodiment, the head 102 tapers from a widest portion near the upper surface of the head to a narrowest portion near the shank 110.

Figure 6:
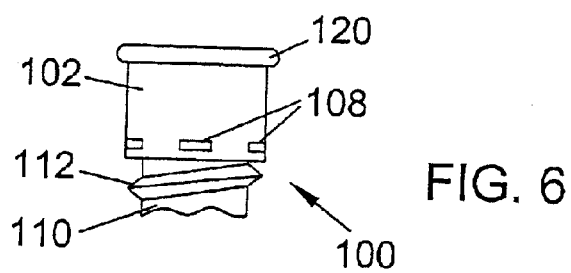
FIG. 6 is a partial front view of a fastener with holes in the fastener head.

FIG. 6 is a side view of the head 102 of an embodiment of fastener 100 showing holes 108 and optional rim 120. Rim 120 may serve to limit the insertion of fastener 100 into a ring 30 during use.

Figure 7:
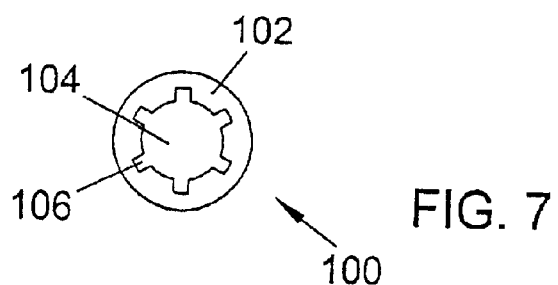
FIG. 7 is a top view of a fastener head having grooves for engaging a locking mechanism.
Figure 8:
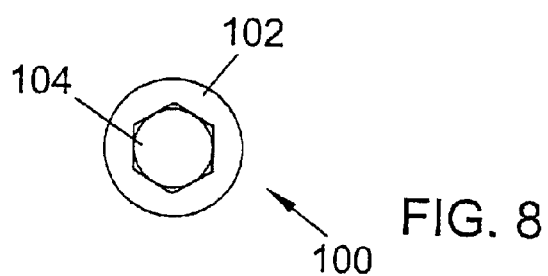
FIG. 8 is a top view of an embodiment of a fastener head with a hexagonal opening and holes to engage a locking mechanism.

FIG. 7 is a top view of the head 102 of a fastener 100 with optional grooves 106. FIG. 8 shows an alternate embodiment of fastener 100 having a hexagonal shape opening 104 and no grooves.

Figure 9:
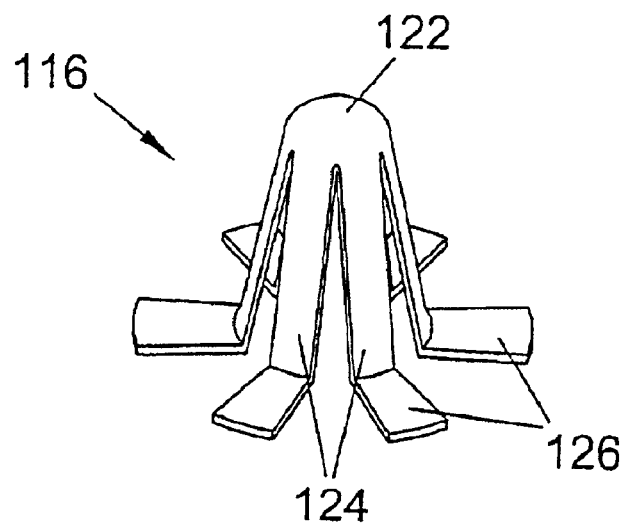
FIG. 9 is a perspective view of a locking mechanism.

FIG. 9 illustrates a locking mechanism 116 used with fastener 100. Locking mechanism 116 includes top 122 with shafts 124 extending downwards and outwards from the top. Prongs 126 are located at ends of shafts 124. Prongs 126 may be substantially parallel to each other and also may be substantially parallel to the locking mechanism top 122. The shafts 124 have a spring-like action which allows the shafts to be compressed. The spring-like action also allows the shafts to return to an original configuration when not compressed.

Figure 10:
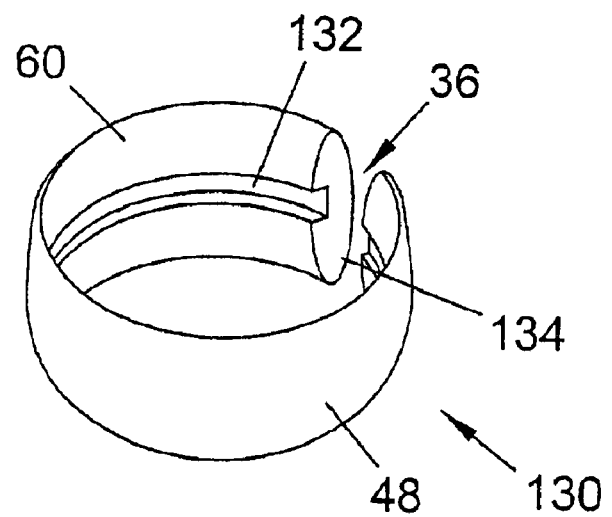
FIG. 10 is a perspective view of a ring that may be used with a fastener and a locking mechanism.

FIG. 10 illustrates an embodiment of a ring 130 that may be used in combination with fastener 100 and locking mechanism 116. Ring 130 includes groove 132. Groove 132 engages prongs 126 on locking mechanism 116 to secure fastener 100 in ring 130 after insertion. Gap 36 in ring 130 allows the ring to contract during insertion of the ring 130 into an end hole 24 of the bone plate 22. Gap 36 also allows ring 130 to be expanded by the head 102 of fastener 100 in the ring 130 to abut the ring against the inner surface 46 of the end hole 24. Abutting the ring 130 against the inner surface 46 of the end hole 24 may fix the position of fastener 32 relative to the bone plate 22.

Figure 11:
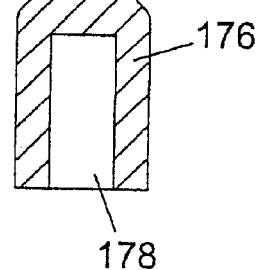
FIG. 11 is a partial sectional view of an insertion/extraction tool for fasteners with locking mechanisms.

FIG. 11 illustrates tool 114. The tool 114 may be used during the insertion and extraction of a fastener 100 and locking mechanism 116. The insertion/extraction tool 114 includes a shaft 172. One end of shaft 172 may include a handle 174 for turning the tool during insertion and removal of a fastener 100. FIG. 11 shows a modified T-handle 174 coupled to the shaft 172, but any type of handle that allows torque to be applied to the fastener during insertion and removal may be used. At an opposite end of shaft 172 from handle 174 is driver head 176. The outer surface of driver head 176 may be shaped to complement the shape of opening 104 in the head of the fastener 100. Driver head 176 may be inserted into the opening 104 of the fastener 100. The fastener may be inserted in an end hole 24 of a bone plate 22 and into a bone by rotating insertion/extraction tool 114. Driver head 176 includes cavity 178. The inner surface of the cavity may slide over and compress the shafts 124 and prongs 126 of a locking mechanism 116.

Figure 12A:
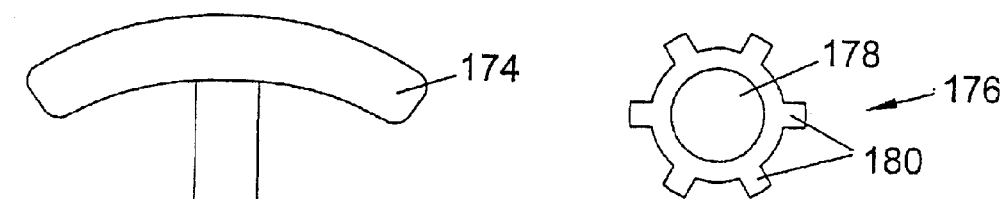
FIG. 12a is a bottom view of a driver head of the insertion/extraction tool shown in FIG. 11. The tool may be used with the fastener head shown in FIG. 7.
Figure 12B:
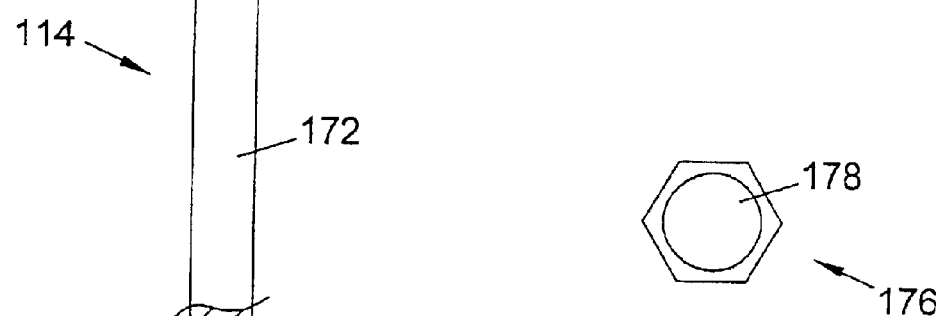
FIG. 12b is a bottom view of the driver head of the insertion and removal tool shown in FIG. 11 which may be used with the fastener head shown in FIG. 8.

FIG. 12a shows a bottom view of an embodiment of a driver head 176 of an insertion/extraction tool 114. The driver head of FIG. 12a may be used with the type of fastener head 102 shown in FIG. 7. The driver head 176 has cavity 178 which allows the driver head to slide over and compress a locking mechanism 116. The driver head 176 includes ridges 180 for engaging complementary grooves 106 in the opening 104 of a fastener head 102. FIG. 12b shows an alternate embodiment of a driver head 176 of an insertion/extraction tool 114. The driver head of FIG. 12b may be used with the type of fastener head 102 shown in FIG. 8. The driver head 176 has cavity 178 which allows the driver head to slide over and compresses a locking mechanism 116. The driver head 176 may be hexagonal shaped to mate with opening 104 of a fastener head 102.

Figure 13:
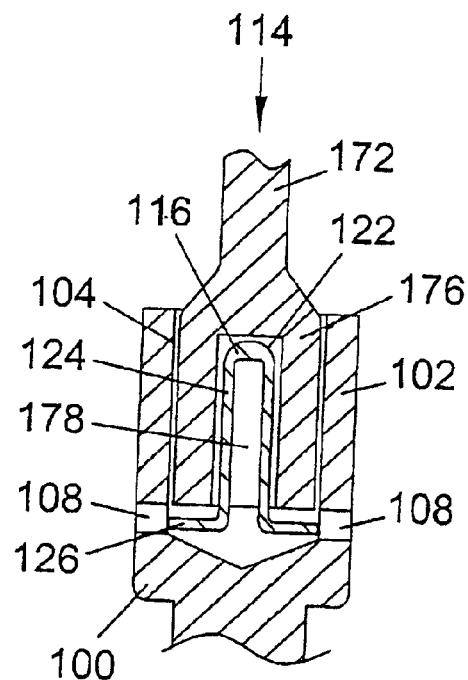
FIG. 13 is a sectional view of a fastener head with an insertion/extraction tool and compressed locking mechanism during an insertion process.

FIG. 13 shows a cross sectional view of an embodiment of a fastener 100, locking mechanism 116, and insertion/extraction tool 114 during the insertion process. Driver head 176 inserts into opening 104 of fastener head 102. Shafts 124 of locking mechanism 116 are compressed within cavity 178 of driver head 176. The compression of shafts 124 causes prongs 126 to retract in holes 108, which allow fastener head 102 to be inserted into a ring 130 without interference by extended prongs 126. When insertion/extraction tool 114 is removed, the shafts 124 uncompress, which causes the prongs 126 to extend out of holes 108.

Figure 14:
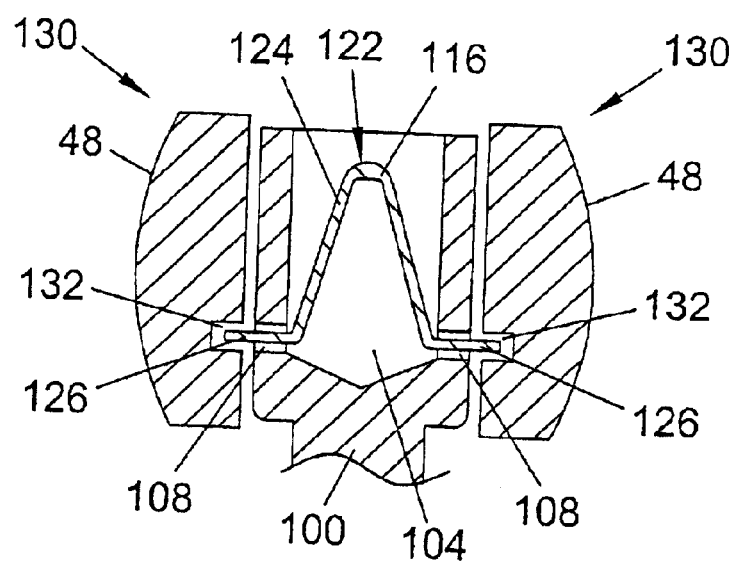
FIG. 14 is a sectional view of a fastener head and locking mechanism inserted into a ring.

FIG. 14 shows a cross sectional view of an embodiment of a fastener 100, locking mechanism 116, and ring 130 after the fastener has been fully inserted in the ring and the insertion/extraction tool 114 has been removed. Shafts 124 of locking mechanism 116 are uncompressed, allowing prongs 126 to extend out of holes 108 in fastener head 102. Prongs 126 extend into groove 132 on the ring 130.

To remove a threaded fastener 100 from ring 130, insertion/extraction tool 114 is inserted in the opening 104 in fastener head 102 to compress the shafts 124 of the locking mechanism 116. Compressing the shafts 124 causes the prongs 126 to retract through holes 108 and removes the connection between the prongs and the ring 130. The tool 114 may then be rotated to remove the fastener 100 from the bone.

After insertion of a fastener 100 and locking mechanism 116 into a bone, if the fastener becomes loose within the bone, fastener backout from the bone plate may be resisted by the locking mechanism-groove connection between locking mechanism 116 and the ring 130. Thus, even if fastener shank 110 loosens within the bone, the fastener head 102 will tend to remain within ring 130 in the hole 24 of the plate 22. There may be some freedom of movement in the connection between the prongs 126 and the groove 130 to allow a fastener 100 to back out slightly from a bone after insertion.

During the surgical procedure for attaching a bone plate to bones using the devices depicted in FIGS. 5–14, holes may be drilled and tapped into the bones to which the bone plate 22 is to be attached. The bone plate 22 may be positioned adjacent to the bones. Rings 130 may be positioned within each end hole 24 before or during the surgical procedure. A fastener 100, with a pre-inserted locking mechanism, may be positioned through a ring 130. An insertion/extraction tool 114 may be inserted in the opening 104 of threaded fastener 100 to compress the locking mechanism 116 within the cavity of the driver head of the tool. Compressing the locking mechanism 116 retracts the prongs 126 of the locking mechanism within the fastener opening 104. The fastener 100 may then be rotated to insert the fastener into a bone. As the fastener 100 is rotated, fastener head 102 moves into the ring 130. Movement of head 102 into ring 130 causes the ring to expand against the end hole 24 to fix the fastener 100 relative to the plate 22. Once the fastener 100 is fully inserted, insertion/extraction tool 114 is removed. Removing the tool 114 causes the locking mechanism 116 to uncompress so that the prongs 126 extend through the holes 108 in the fastener head 102 and engage the groove 132 in the ring 130. Fasteners 100 may be inserted through the remaining end holes 24 and into bone to securely attach the plate 22 to the bones.

FIG. 15 illustrates an embodiment of a fastener 200 with fastener head 202 having groove 204. When a fastener 200 is inserted through a ring 230 positioned in a plate 22, the groove 204 may engage fingers 232 on the ring (the ring shown in FIGS. 19 and 20) to secure the fastener 200 within the ring. Fastener 200 may include the head 202 and shank 206 with threading 208. Head 202 may include opening 210 configured to accept a drive tool.

The engagement of a finger 232 of a ring 230 on groove 204 may inhibit fastener 200 from backing out of the ring after insertion of the fastener into the plate 22. In an embodiment, the outer surface of head 202 is substantially cylindrical. In another embodiment, as shown in FIG. 16, the head 202 may taper. The widest portion of the head 202 may be near the top surface of the head, and the narrowest portion may be near the shank 206.

FIG. 17 illustrates an embodiment of a fastener 200 which has radial slots 212 extending from the outer surface of the head into the opening 210. The radial slots 212 may allow a portion of head 202 to contract during insertion. The radial slots 212 may also be used to engage a portion of a drive head of an insertion/extraction tool (not shown).

FIGS. 15, 16, and 17 illustrate fastener heads 202 wherein the grooves 204 are rims along top edges of the heads. FIG. 18 illustrates an embodiment of a fastener 200 wherein the groove 204 is located at a position along the side of the fastener head 202. The groove 204 may be located at any position along the side of the fastener head 202. When the fastener head 202 is driven through a ring 230, the interaction of the fastener head, the ring, and the end hole 24 allows fingers 232 of the ring to snap into the groove 214. The fingers 232 may secure the fastener head 202 to the ring 230.

Figure 19:
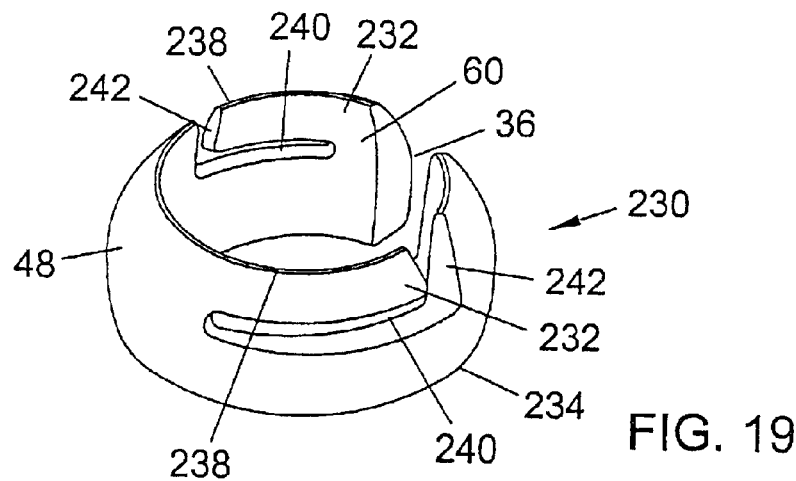
FIG. 19 is a perspective view of an embodiment of a ring.
Figure 20:
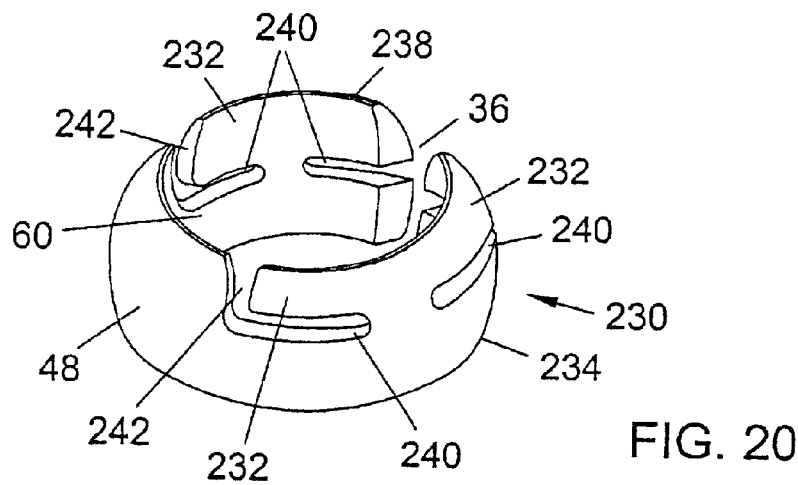
FIG. 20 is a perspective view of an embodiment of a ring.

FIGS. 19 and 20 show perspective views of embodiments of ring 230 that may be used with fasteners having a groove. Ring 230 may include bottom 234, top 238, an outer surface 48, an inner surface 60, gap 36, and slots 240 and notches 242. The slots 240 and notches 240 may form the fingers 232. Gap 36 may allow ring 230 to contract. Contraction of the ring 230 may facilitate the insertion of the ring into an end hole 24 in a bone plate 22. Gap 36 may also allow the ring 230 to expand against the end hole 24 when a fastener head 202 passes into the ring. Expansion of the ring against the end hole 24 fixes the fastener 200 relative to the bone plate 22.

In some embodiments, outer surface 48 of the ring 230 may be textured to increase the coefficient of friction between ring 230 and the hole 24. In some embodiments, inner surface 60 of the ring 230 may be tapered to match a tapered head of a fastener 200. Having tapered surfaces may facilitate the expansion of ring in an end hole 24 during insertion of the fastener into the spinal plating system 20.

The shape of the end hole 24 may push the fingers 232 inwards past the edge of the groove 204 of a fastener 200 when the groove is inserted into a ring 230 so that the groove passes an upper edge of the ring slots 240. The inward positioned fingers 232 may inhibit fastener 200 from backing out of the ring 230 and the end hole 24. When the fastener 200 is inserted into the ring 230, the fastener head 202 may expand the outside surface 48 of the ring against the inner surface 46 of the end hole 24 to fix the fastener 200 to the ring, and the ring to the plate 22.

Figure 21:
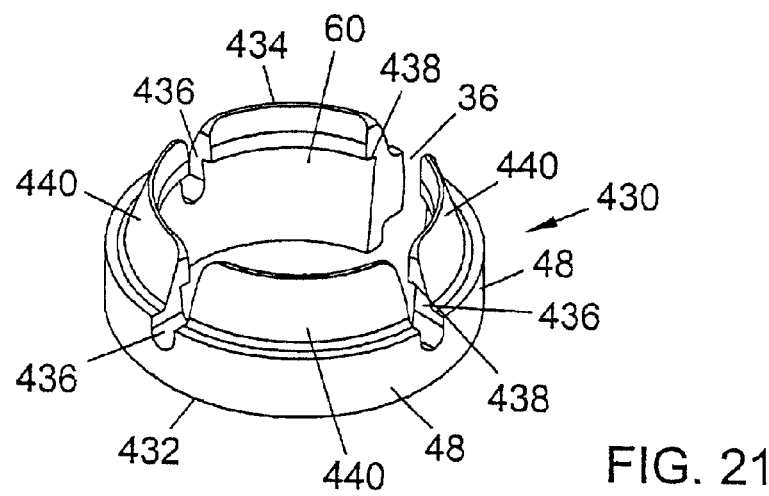
FIG. 21 is a perspective view of an embodiment of a ring.

FIG. 21 is a perspective view of an embodiment of a ring that may be used with fasteners 200 that have rims 204, such as the fasteners shown in FIG. 15–17. Ring 430 may include bottom 432, top 434, outer surface 48, inner surface 60, gap 36, notches 436, and ridges 438. Notches 436 divide the ring 430 into segments or paddles 440. Notches 436 and gap 36 may allow ring 430 to contract, facilitating the insertion of the ring into an end hole 24 of a bone plate 22. Notches 436 and gap 36 may also allow ring 430 to expand when a fastener head 202 passes into the ring to fix the position of the fastener relative to the bone plate 22. Notches 436 may also allow paddles 436 to bend outwards during insertion of a fastener 200. The outer surface 48 and/or the inner surface 60 may be textured. The inner surface of the ring 430 may be tapered to correspond to the taper of a fastener head 202.

Figure 22:
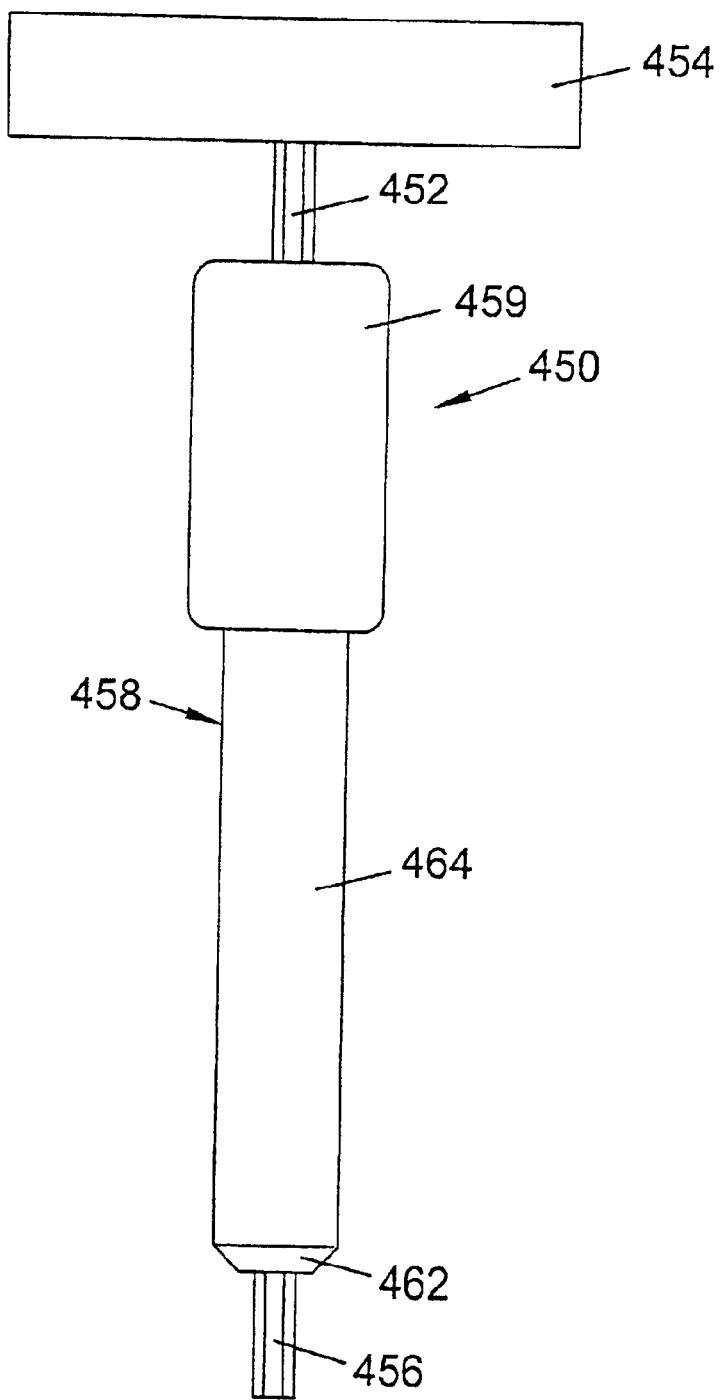
FIG. 22 is front view of an insertion/extraction tool which may be used with the ring of FIG. 21.

FIG. 22 illustrates an embodiment of an insertion tool/extraction tool 450 for use with a fastener 200 and ring 430. Insertion/extraction tool 450 may include shaft 452, handle 454, driver head 456, and extraction member 458. At one end of shaft 452 is handle 454 for turning the tool during insertion and removal of a fastener 200. The illustration shows a T-handle, but any other type of handle that allows sufficient torque to be applied to the fastener 200 to allow for insertion or removal of the fastener may be used. At the opposite end of shaft 452 from handle 454 is driver head 456. The outer surface of driver head 456 may be shaped complementary to the shape of the opening 210 in the head 202 of the fastener 200.

The extraction member 458 shown in FIG. 22 may include grip 459, passage 460, (shown in FIG. 23c), tip 462, and extraction head 464. The passage 460 extends through the grip 459 and the extraction head 464. During the insertion process, extraction member 458 may be removed from shaft 452. To extract a fastener from a ring 430, extraction member 458 may be slid back on to shaft 452. Driver head 456 is inserted into the opening 210 of the fastener 200. Extraction member 458 slides down shaft 452 until tip 462 of extraction head 464 contacts the top of the ring 430. Downwards pressure on the extraction member 458 forces paddles 440 of the ring 430 outwards, and disengages the ridge 438 on the paddles 440 from the rim 204 on the fastener head 202. The fastener 200 may then be backed out of the plate 22 by rotating the shaft 452 with the handle 454. Preferably, rotating shaft 452 does not rotate the extraction member 458.

Figure 23A:
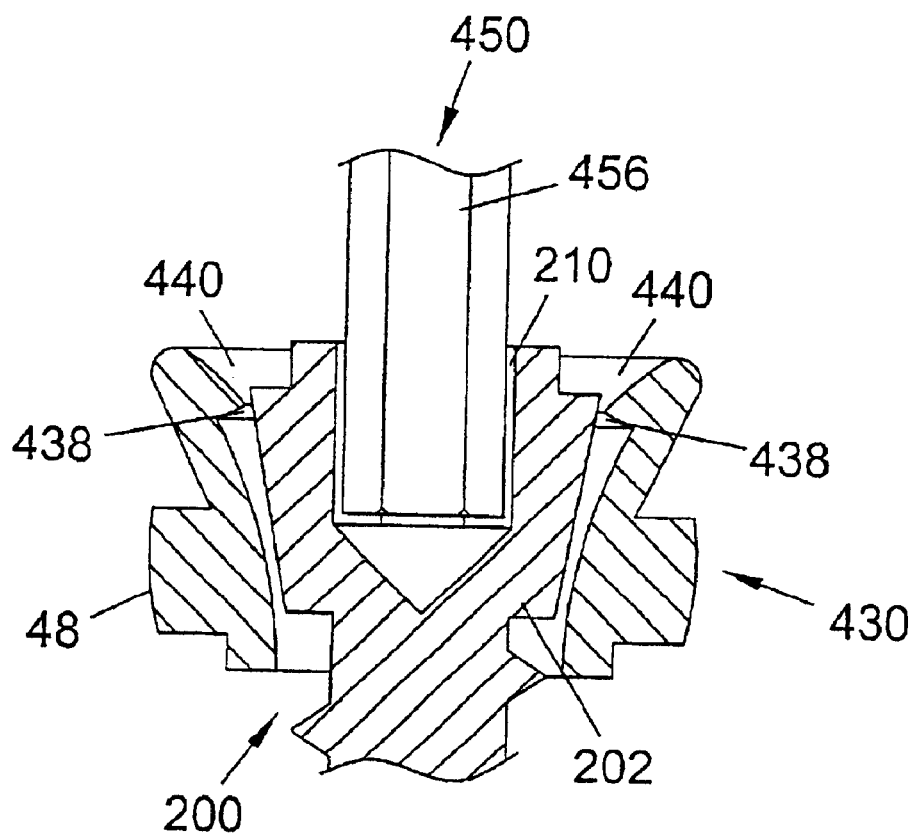
FIG. 23a is a partial cross sectional view of a fastener during insertion in the ring of FIG. 21. The shaft of the insertion/extraction tool is not shown in cross section.
Figure 23B:
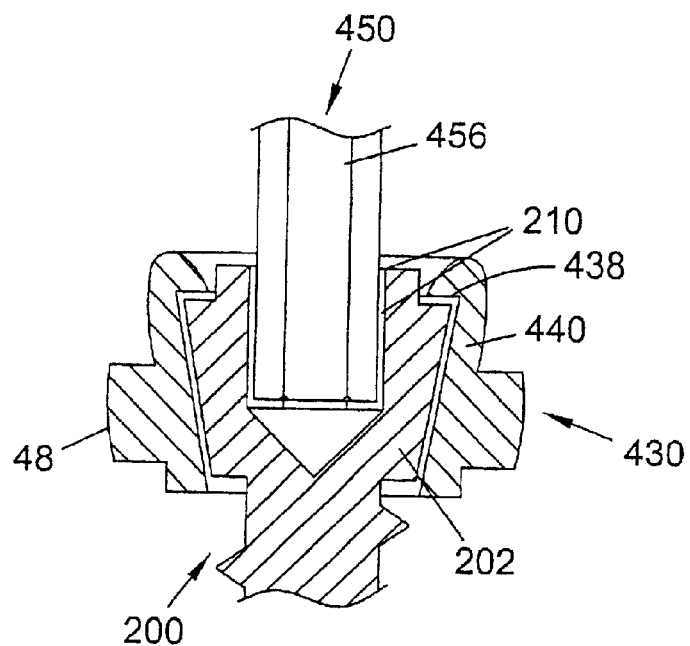
FIG. 23b is a partial cross sectional view of a fastener after insertion in the ring of FIG. 21. The shaft of the insertion/extraction tool is not shown in cross section.
Figure 23C:
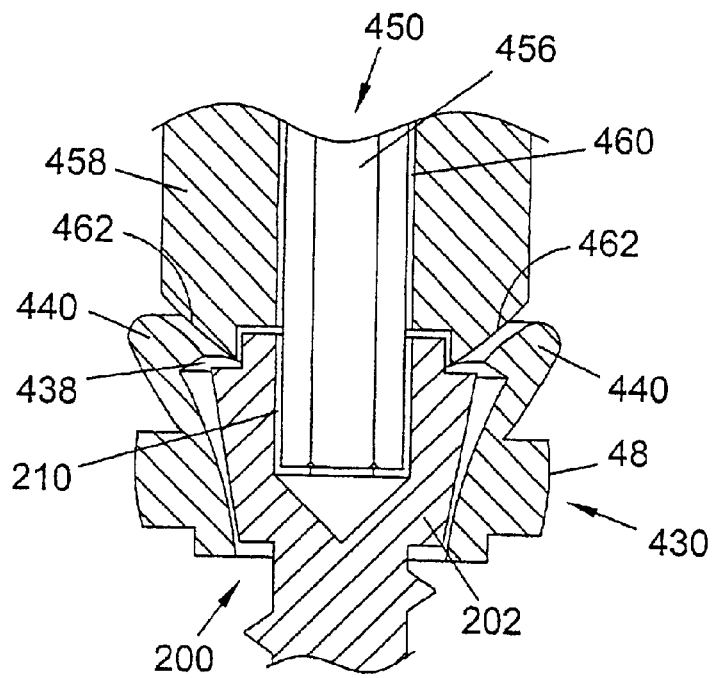
FIG. 23c is a partial cross sectional view of a fastener during removal from the ring of FIG. 21. The shaft of the insertion/extraction tool is not shown in cross section.

FIG. 23a, 23b, and 23c show partial cross sectional views of a threaded fastener 200, ring 430, and insertion/extraction tool 450 during the insertion and extraction processes. Referring to FIG. 23a, driver head 456 of insertion/extraction tool 450 is inserted in opening 210 of fastener head 202. Ring 430 is positioned inside an end hole 24 in a bone plate and the bone plate is positioned on a bone (bone and bone plate not shown). Fastener 200 is screwed into the bone until the outer surface of fastener head 202 contacts the surfaces of the paddles 440. The tapering of the outer surface of fastener head 202 provides a ramping force on the surfaces of the paddles 440, to bend the paddles outwards as fastener 200 is screwed farther into the bone.

In FIG. 23b, fastener 200 has been screwed in to the desired depth. Fastener head 202 penetrates ring 430 far enough to allow ridges 438 to snap onto rim 204 on fastener head 202. Driver head 456 of insertion/extraction tool 450 is shown still inserted in opening 210 prior to removal from the opening. After insertion, if the fastener 200 becomes loose within the bone, fastener backout from the bone plate may be resisted by the ridge-rim connection between fastener head 202 and ring 430. Thus, even if the fastener shank loosens within the bone, the fastener head 202 will tend to remain within ring 430 in the end hole 24 of the plate 22 so as not to protrude from the plate into surrounding body tissue. In some embodiments, there may be some freedom of movement in the connection between the ridges 438 on the paddles 440 and the rim 204 to allow a fastener 200 to back out slightly from a bone after insertion. Typically, the freedom of movement is limited so that the fastener head 202 may not protrude from the plate 22.

FIG. 23c shows insertion/extraction tool 250 being used to remove a fastener 200. Driver head 256 is inserted in opening 210 of fastener 200. Extraction head 464 is slid down shaft 452 of insertion/extraction tool 450 until the sloped surface of tip 462 applies a wedging force against the sloped upper surfaces of paddles 440. The wedging force bends the paddles 440 outwards to disengage the ridges 438 from the rim 204. Fastener 200 may then be backed out of the bone, the ring 430 and the plate 22.

The plate, fasteners, and locking mechanisms may be made of steel (e.g, stainless steel), titanium, steel alloys or titanium alloys. These materials are generally nontoxic, bio-compatible, strong, and non-corrosive. Other materials that have these properties may also be used. The plate and the rings may be made of a number of bio-compatible materials including metals, plastics, and composites.

Any of the embodiments described above may be used individually or in combination with other embodiments described above. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A bone stabilization system, comprising:
   a plate;
   an opening through the plate;
   a ring positionable within the opening, the ring comprising a plurality of paddles; and
   a fastener positionable through the ring, the fastener configured to couple the plate to bone;
   wherein the paddles of the ring are configured to move outwards to allow a portion of the fastener to be positioned in the opening, and wherein the paddles are configured to move inwards after insertion of a portion of the fastener to inhibit removal of the fastener from the plate.

2. The system of claim 1, wherein the ring further comprises a curved outer surface to conform to a curved inner surface of the opening.

3. The system of claim 1, wherein an outer surface of the ring complements at least a portion of an inner surface of the opening.

4. The system of claim 1, wherein an inner surface of the ring complements at least a portion of an outer surface of the fastener.

5. The system of claim 1, wherein a portion of the ring engages a portion of a head of the fastener.

6. The system of claim 1, wherein the fastener comprises a groove to engage the paddles of the ring.

7. The system of claim 6, wherein the groove comprises a rim formed along an edge of the fastener.

8. The system of claim 1, wherein a diameter of a portion of the head is greater than a diameter of an inner surface of the ring such that the head exerts an expanding force on the ring when positioned in the ring.

9. The system of claim 1, wherein the paddles of the ring comprise ridges that are configured to engage a surface of the fastener.

10. The system of claim 1, wherein an outer width of the ring is greater than a width of the opening proximate an upper surface and a lower surface of the plate such that removal of the ring positioned within the opening is inhibited.

11. The system of claim 1, wherein the ring further comprises a gap to allow the ring to expand and contract.

12. The system of claim 11, wherein contracting the gap of the ring allows insertion of the ring into the opening of the plate.

13. The system of claim 1, wherein the ring is configured to move within the opening of the plate to allow a shank of the fastener to be inserted into bone at an oblique angle to the plate.

14. The system of claim 1, wherein the ring is configured to rotate within the opening when the fastener is positioned through the ring.

15. The system of claim 1, further comprising a second fastener positioned through a second ring positioned within a second opening in the plate such that the two fasteners extend through the plate in diverging directions relative to each other.

16. The system claim 1, further comprising a second fastener positioned through a second ring positioned within a second opening in the plate such that the two fasteners extend through the plate in converging directions relative to each other.

17. A system for stabilizing two bone portions, comprising;
 a plate;
 an opening through the plate;
 a ring positionable within the opening, the ring comprising deflectable portions; and
 a fastener positionable through the ring, the fastener configured to couple the plate to bone;
 wherein the deflectable portions of the ring are configured to deflect outwards to allow a portion of the fastener to be positioned in the opening, and wherein the deflectable portions are configured to deflect inwards such that removal of the fastener from the plate is inhibited during use.

18. They system of claim 17, wherein the ring further comprises a curved outer surface to conform to a curved inner surface of the opening.

19. The system of claim 17, wherein an outer surface of the ring complements at least a portion of an inner surface of the opening.

20. The system of claim 17, wherein an inner surface of the ring complements at least a portion of an outer surface of the fastener.

21. The system of claim 17, wherein the deflectable portions of the ring are formed by a plurality of notches in the ring.

22. The system of claim 17, wherein a portion of the ring engages a portion of a head of the fastener.

23. The system of claim 17, wherein the fastener comprises a groove to engage the deflectable portions of the ring.

24. The system of claim 23, wherein the groove comprises a rim formed along an edge of the fastener.

25. The system of claim 17, wherein the deflectable portions of the ring comprise ridges, and wherein the ridges extend into a groove in the fastener.

26. The system of claim 17, wherein a diameter of a portion of the head is greater than a diameter of an inner surface of the ring such that the head exerts an expanding force on the ring when positioned in the ring.

27. The system of claim 17, wherein the deflectable portions of the ring comprise ridges that are configured to engage a top surface of the head of the fastener.

28. The system of claim 17, wherein an outer width of the ring is greater than a width of the opening proximate an upper surface and a lower surface of the plate such that removal of the ring positioned within the opening is inhibited.

29. The system of claim 17, wherein the ring further comprises a gap to allow the ring to expand and contract.

30. The system of claim 29, wherein contracting the gap of the ring allows insertion of the ring into the opening of the plate.

31. The system of claim 17, wherein the ring is configured to move within the opening of the plate to allow a shank of the fastener to be inserted into bone at an oblique angle to the plate.

32. The system of claim 17, wherein the ring is configured to rotate within the opening when the fastener is positioned through the ring.

33. The system of claim 17, further comprising a second fastener positioned through a second ring positioned within a second opening in the plate such that the two fasteners extend through the plate in diverging directions relative to each other.

34. The system of claim 17, further comprising a second fastener positioned through a second ring positioned within a second opening in the plate such that the two fasteners extend through the plate in converging directions relative to each other.

35. A bone stabilization system, comprising:
 a plate;
 an opening through the plate;
 a ring positionable within the opening, the ring comprising:
  a lower portion; and
  an upper portion, the upper portion comprising fingers extending from the lower portion, wherein the fingers are substantially parallel to the lower portion; and
 a fastener positionable through the ring, the fastener comprising a head;
 wherein the fingers of the ring are configured to engage a portion of the head of the fastener to inhibit removal of the fastener from the plate during use.

36. The system of claim 35, wherein the ring further comprises a curved outer surface to conform to a curved inner surface of the opening.

37. The system of claim 35, wherein an outer surface of the ring complements at least a portion of an inner surface of the opening.

38. The system of claim 35, wherein an inner surface of the ring complements at least a portion of an outer surface of the fastener.

39. The system of claim 35, wherein the portion of the head of the fastener comprises a groove.

40. The system of claim 39, wherein the groove comprises a rim formed along an edge of the fastener head.

41. The system of claim 35, wherein the upper portion of the ring further comprises a ridge, and wherein the ridge extends into a groove in the head of the fastener.

42. The system of claim 35, wherein a diameter of the head is greater than a diameter of an inner surface of the ring such that the head exerts an expanding force on the ring when positioned in the ring.

43. The system of claim 35, wherein an outer width of the ring is greater than a width of the opening proximate an upper surface and a lower surface of the plate such that removal of the ring positioned within the opening is inhibited.

44. The system of claim 35, wherein the ring further comprises a gap to allow the ring to expand and contract.

45. The system of claim 44, wherein contracting the gap of the ring allows insertion of the ring into the opening of the plate.

46. The system of claim 35, wherein the upper portion of the ring further comprises a ridge that is configured to engage a top surface of the head of the fastener to limit an insertion depth of the fastener.

47. The system of claim 35, wherein the ring is configured to move within the opening of the plate to allow a shank of the fastener to be inserted into bone at an oblique angle to the plate.

48. The system of claim 35, wherein the ring is configured to rotate within the opening when the fastener is positioned through the ring.

49. The system of claim 35, further comprising a second fastener positioned through a second ring positioned within a second opening in the plate such that the two fasteners extend through the plate in diverging directions relative to each other.

50. The system of claim 35, further comprising a second fastener positioned through a second ring positioned within a second opening in the plate such that the two fasteners extend through the plate in converging directions relative to each other.

51. A method for stabilizing bone, comprising:
placing a ring within a plate, wherein the ring comprises paddles;
positioning the plate adjacent to bone;
inserting a fastener into the bone through the ring in the plate; and
coupling the fastener to the ring with the paddles of the ring to inhibit removal of the fastener from the plate.

52. The method of claim 51, wherein an outer width of the ring is greater than a width of the opening proximate an upper surface and a lower surface of the plate such that removal of the ring positioned within the opening is inhibited.

53. The method of claim 51, wherein the ring is configured to move within the opening of the plate to allow a shank of the fastener to be inserted into bone at an oblique angle to the plate.

54. The method of claim 51, wherein the ring is configured to rotate within the opening when the fastener is positioned through the ring.

55. The method of claim 51, further comprising inserting a second fastener through a second ring positioned within a second opening in the plate such that the two fasteners extend through the plate in diverging directions relative to each other.

56. The method of claim 51, further comprising inserting a second fastener through a second ring positioned within a second opening in the plate such that the two fasteners extend through the plate in converging directions relative to each other.

57. A method for stabilizing bone, comprising:
positioning a ring within an opening of a plate, wherein the ring comprises a lower portion and an upper portion, the upper portion comprising fingers extending from and substantially parallel to the lower portion;
positioning a head of a fastener within the ring; and
engaging the head of the fastener with the fingers of the ring to inhibit removal of the fastener from the plate.

58. The method of claim 57, wherein an outer width of the ring is greater than a width of the opening proximate an upper surface and a lower surface of the plate such that removal of the ring positioned within the opening is inhibited.

59. The method of claim 57, wherein the ring is configured to move within the opening of the plate to allow a shank of the fastener to be inserted into bone at an oblique angle to the plate.

60. The method of claim 57, wherein the ring is configured to rotate within the opening when the fastener is positioned through the ring.

61. The method of claim 57, further comprising inserting a second fastener through a second ring positioned within a second opening in the plate such that the two fasteners extend through the plate in diverging directions relative to each other.

62. The method of claim 57, further comprising inserting a second fastener through a second ring positioned within a second opening in the plate such that the two fasteners extend through the plate in converging directions relative to each other.

* * * * *